(12) United States Patent
Heismann et al.

(10) Patent No.: US 7,158,611 B2
(45) Date of Patent: Jan. 2, 2007

(54) METHOD FOR DETERMINING DENSITY DISTRIBUTIONS AND ATOMIC NUMBER DISTRIBUTIONS DURING RADIOGRAPHIC EXAMINATION METHODS

(75) Inventors: Björn Heismann, Erlangen (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 181 days.

(21) Appl. No.: 10/488,397

(22) PCT Filed: Aug. 21, 2002

(86) PCT No.: PCT/DE02/03055

§ 371 (c)(1),
(2), (4) Date: Mar. 3, 2004

(87) PCT Pub. No.: WO03/024331

PCT Pub. Date: Mar. 27, 2003

(65) Prior Publication Data

US 2004/0223585 A1    Nov. 11, 2004

(30) Foreign Application Priority Data

Sep. 3, 2001   (DE) ................................. 101 43 131

(51) Int. Cl.
*G01N 23/087* (2006.01)

(52) U.S. Cl. ........................................ 378/98.9; 378/53
(58) Field of Classification Search ................ 378/5, 378/16, 53, 57, 98.9, 98.11
See application file for complete search history.

(56) References Cited

U.S. PATENT DOCUMENTS 4,029,963 A * 6/1977 Alvarez et al. ................ 378/5

(Continued)

FOREIGN PATENT DOCUMENTS

WO    WO 97/24069    7/1997

OTHER PUBLICATIONS

L. A. Lehmann, R. E. Alvarez, A. Macovski, and W. R. Brody. Generalized Image Combinations in Dual KVP Digital Radiography. Med. Phys. 8(5), 659-667 (1981).*

(Continued)

*Primary Examiner*—Allen C. Ho
(74) *Attorney, Agent, or Firm*—Harness, Dickey & Pierce, P.L.C.

(57) ABSTRACT

The functional dependency of a first X-ray absorption value of density and atomic number is determined in the instance of a first X-ray spectrum, and at least the functional dependency of a second X-ray absorption value of density and atomic number is determined in the instance of a second X-ray spectrum. Based on a recording of a first distribution of X-ray absorption values of the object to be examined in the instance of a first X-ray spectrum, and on a recording of at least one second distribution of X-ray absorption values of the object to be examined in the instance of a second X-ray spectrum, the values for density and atomic number are determined by comparing the functional dependency of a first X-ray absorption value of the first distribution of X-ray absorption values with the functional dependency(ies) of the X-ray absorption values, which are assigned to the first X-ray absorption value, of the second and/or other distributions of X-ray absorption values.

29 Claims, 5 Drawing Sheets

U.S. PATENT DOCUMENTS

| | | | | |
|---|---|---|---|---|
| 4,149,081 A | * | 4/1979 | Seppi | 378/5 |
| 4,626,688 A | * | 12/1986 | Barnes | 250/361 R |
| 4,686,695 A | * | 8/1987 | Macovski | 378/146 |
| 4,995,107 A | | 2/1991 | Klingenbeck | 378/7 |
| 5,123,037 A | * | 6/1992 | Picard et al. | 378/98.2 |
| 5,247,559 A | * | 9/1993 | Ohtsuchi et al. | 378/53 |
| 5,379,333 A | * | 1/1995 | Toth | 378/16 |
| 5,524,133 A | | 6/1996 | Neale et al. | 378/53 |
| 5,600,700 A | * | 2/1997 | Krug et al. | 378/57 |
| 5,661,774 A | * | 8/1997 | Gordon et al. | 378/101 |
| 5,917,877 A | * | 6/1999 | Chiabrera et al. | 378/207 |
| 6,195,413 B1 | * | 2/2001 | Geus et al. | 378/98.9 |
| 6,418,189 B1 | * | 7/2002 | Schafer | 378/57 |
| 6,445,765 B1 | * | 9/2002 | Frank et al. | 378/56 |
| 6,574,302 B1 | * | 6/2003 | Adriaansz | 378/54 |
| 6,597,759 B1 | * | 7/2003 | Mazess et al. | 378/53 |
| 6,997,610 B1 | * | 2/2006 | Heismann | 378/207 |
| 2003/0147502 A1 | * | 8/2003 | Heismann et al. | 378/156 |
| 2005/0084063 A1 | * | 4/2005 | Heismann et al. | 378/53 |

OTHER PUBLICATIONS

Robert E. Alvarez and Albert Macovski. Energy-Selective Reconstructions in X-Ray Computerized Tomography. Phys. Med. Biol. 21 (5), 733-744 (1976).*

Materialselektive Bildgebung und Dichtemessung mit der Zwei-Spektren-Methode, I. Grundlagen und Methodik, W. Kalender, W. Bautz, D. Felsenberg, C. Süß und E. Klotz, Digit. Bildiagn. 7, 1987, 66-77, Georg Thieme Verlag.

* cited by examiner

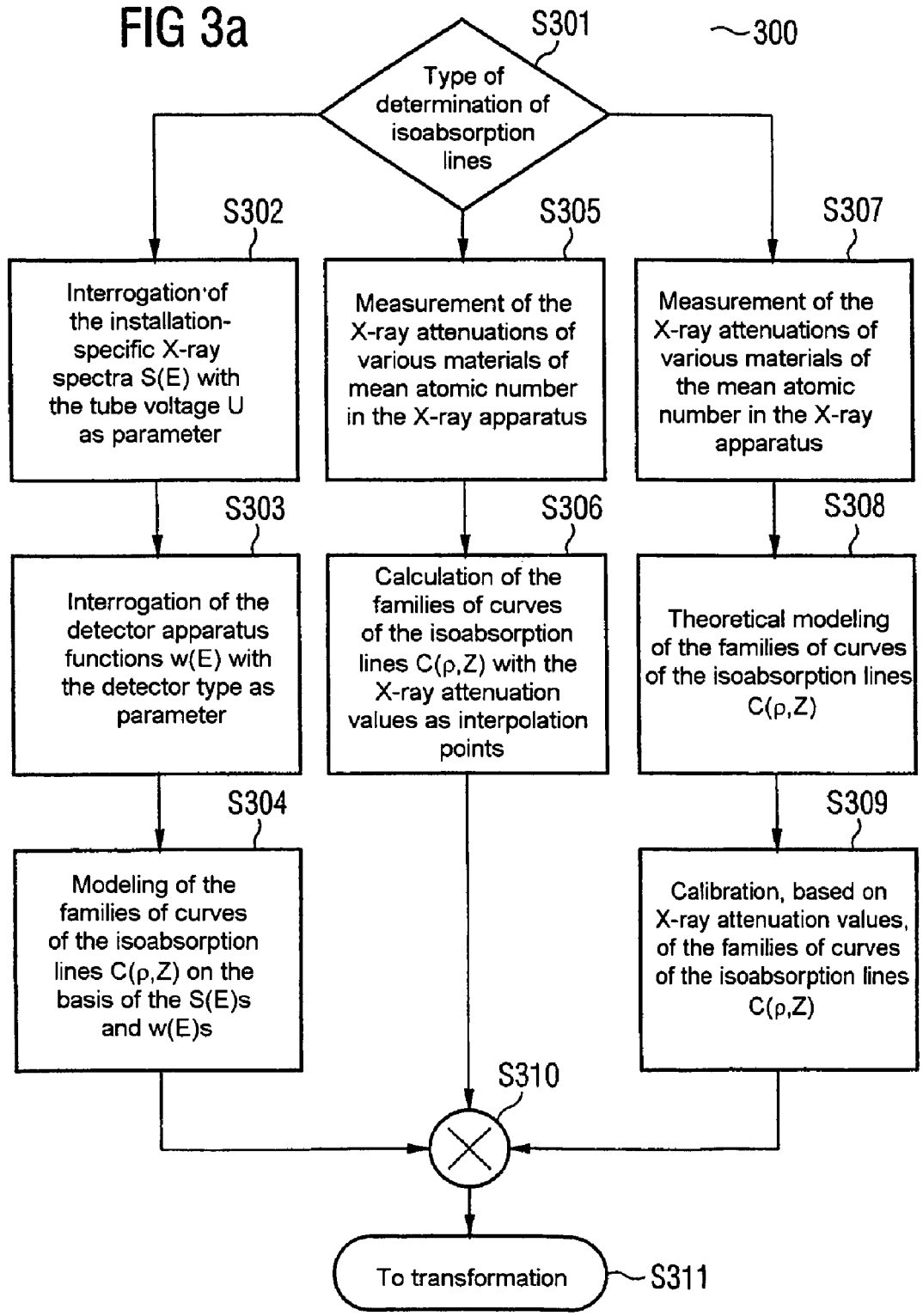

METHOD FOR DETERMINING DENSITY DISTRIBUTIONS AND ATOMIC NUMBER DISTRIBUTIONS DURING RADIOGRAPHIC EXAMINATION METHODS

This application is the national phase under 35 U.S.C. § 371 of PCT International Application No. PCT/DE02/03055 which has an International filing date of Aug. 21, 2002, which designated the United States of America and which claims priority on German Patent Application number DE 101 43 131.7 filed Sep. 3, 2001, the entire contents of which are hereby incorporated herein by reference.

FIELD OF THE INVENTION

The present invention generally relates to a method, an X-ray apparatus and a computer software product for ascertaining image data relating to the distribution of physically and chemically relevant data in objects of human or animal type that are to be examined, or from the field of materials testing or safety testing. The invention relates in particular to separating radiographic image data into a distribution of the material density and a distribution of the atomic number in the object to be examined.

BACKGROUND OF THE INVENTION

The result of all radiographic methods such as, for example, computed tomography, mammography, angiography, X-ray inspection technology or comparable methods is the representation of the attenuation of an X-ray beam along its path from the X-ray source to the X-ray detector. This attenuation is caused by the transradiated media or materials along the beam path. The attenuation is usually defined as the logarithm of the ratio of the intensity of the attenuated radiation to the primary radiation, and denoted, with reference to the path normal, as attenuation coefficient of the material.

A multiplicity of radiographic examination units use not the attenuation coefficient, but a value normalized to the attenuation coefficient of water, the CT number, in representing the attenuation distribution of an X-ray beam in an object to be examined. This number is calculated from an attenuation coefficient $\mu$ currently determined by a measurement, and the reference attenuation coefficient $\mu_{H_2O}$ according to the following equation:

$$C = 1000 \times \frac{\mu - \mu_{H_2O}}{\mu_{H_2O}} \quad [HU] \tag{1}$$

where the CT number C is expressed using the Hounsfield unit [HU]. A value of $C_{H_2O}=0$ HU results for water, and a value of $C_L=-1000$ HU for air.

Since both representations can be transformed into one another, or are equivalent, the generally selected term of attenuation value denotes both the attenuation coefficient $\mu$ and the CT value in what follows. Furthermore, the terms of material and tissue are used interchangeably in the substantive context of this description of the embodiments of invention. It is assumed that a material within the context of a medically indicated examination can be an anatomical tissue, and, conversely, that in testing of materials and in safety testing a tissue is to be understood as any desired material of an object to be examined.

Increased attenuation values can be ascribed either to materials of higher atomic number such as, for example, calcium in the skeleton or iodine in a contrast medium, or to an increased density of soft parts such as, for example, in the case of a lung nodule. The local attenuation coefficient $\mu$ at the location $\vec{r}$ is a function of the X-ray energy E irradiated into the tissue or material, and of the local density $\rho$ of tissue or material in accordance with the following equation:

$$\mu = \mu(E, \vec{r}) = \left(\frac{\mu}{\rho}\right)(E) \times \rho(\vec{r}) \tag{2}$$

with the mass attenuation coefficient $$\left(\frac{\mu}{\rho}\right)(E)$$

dependent on energy and material.

The energy-dependent X-ray absorption of a material, as is defined by its effective atomic number, is thus superimposed on the X-ray absorption that is influenced by the material density. Materials or tissues of different chemical or physical composition may thus have identical attenuation values in the X-ray image. Conversely, on the other hand, it is impossible to deduce the material composition of an object to be examined from the attenuation value in an X-ray picture.

Correct interpretation of the distribution—thus actually rather unclear—of the X-ray attenuation values in an X-ray image produced using a radiographic examination method can generally be carried out only on the basis of morphological criteria in the medical sector, and generally requires a radiologist with decades of experience in his field. Nevertheless, in some circumstances, structures which occur with increased attenuation values in the imaging process for an X-ray examination cannot be clearly classified. For example, it is difficult to distinguish between calcification close to the hilus on a thorax overview picture and a vessel which is located orthogonally with respect to the imaging plane. It is also virtually impossible to distinguish, for example, between diffuse calcification and fresh bleeding.

Even in the case of materials testing and safety testing, the tester generally supplements the information in the display of an attenuation value distribution by his personal specialist knowledge and professional experience. Nevertheless, it is impossible, for example, for him to distinguish reliably between plastic-bonded explosive mixtures and a non-explosive plastic directly from an X-ray image.

Methods for displaying material-characteristic values are required for this purpose. In "Materialselektive Bildgebung und Dichtemessung mit der Zwei-Spektren-Methode, I. Grundlagen und Methodik, W. Kalender, W. Bautz, D. Felsenberg, C. Süß und E. Klotz, Digit. Bildiagn. 7, 1987, 66–77, Georg Thieme Verlag" ["Material-selective imaging and density measurement with the aid of the two-spectra method, I. Fundamentals and Methodology, W. Kalender, W. Bautz, D. Felsenberg, C. Süß and E. Klotz, Digit. Bilddiagn. 7, 1987, pages 66–77, Georg Thieme Verlag"], W. Kalender et al. describe a method for base material decomposition in the case of X-ray pictures. The method is based on the effect that materials and tissues of higher atomic number absorb low-energy X-radiation substantially more intensely than do materials or tissues of lower atomic number. By contrast, in the case of higher X-ray beam energies the attenuation values become assimilated and are largely a function of the material density.

Unless otherwise indicated, in the context of this description the term of atomic number is not used in the strict sense relating to the elements, but instead denotes an effective atomic number of a tissue, or material, that is calculated from the chemical atomic numbers and atomic weights of the elements which are involved in the formation of the tissue or material.

In the method proposed by W. Kalender et al., the X-ray attenuation values of an object to be examined are measured with the aid of X-ray beams of lower and higher energy, and the values obtained are compared with the corresponding reference values of two base materials such as, for example, calcium (for skeletal material) and water (for soft part tissues). It is assumed that each measured value can be represented as a linear superposition of the measured values of the two base materials. For example, a skeletal component and a soft tissue component can be calculated for each element of the pictorial display of the object to be examined from the comparison with the values of the base materials, the result being a transformation of the original pictures into displays of the two base materials of skeletal material and soft part tissue.

The base material decomposition or the two-spectrum method is therefore suitable for distinguishing between anatomical structures in human and animal tissues with a strongly differing atomic number. In materials testing and safety testing, it would therefore be possible, for example, to distinguish according to predefined types of materials, so-called material classes. The aim of the base material decomposition is not a functional display that permits detection of the physical and chemical characteristics of the materials examined, or variations in these characteristics within a type of material.

SUMMARY OF THE INVENTION

It is therefore an object of an embodiment of the present invention to propose a method, an X-ray apparatus and a computer software product that provide chemically and physically relevant information relating to an object to be examined on the basis of radiographically provided absorption data of the object to be examined.

An object may be achieved by a method for determining the distributions of density and atomic number in an object to be examined, having the steps of recording a first distribution of X-ray absorption values of the object to be examined for a first X-ray spectrum, and of recording at least a second distribution of X-ray absorption values of the object to be examined for a second X-ray spectrum, in order to determine a first functional dependence of a first X-ray absorption value of the first distribution of X-ray absorption values on density and atomic number, and in order to determine a second functional dependence of a second X-ray absorption value, assigned to the first X-ray absorption value, of the second distribution of X-ray absorption values on density and atomic number, and in order to ascertain a value for the density and the atomic number from a comparison of the first functional dependence with the second functional dependence and/or further functional dependences.

The term "X-ray spectrum" used in the context of this document has a further-ranging meaning than only the spectral distribution of an X-radiation emitted by the X-ray source of the apparatus. Different spectral components of a radiation having different degrees of efficiency are converted on the part of the X-ray detectors, and thereby differently weighted. The effective spectral distribution resulting therefrom is denoted in this document as X-ray spectrum.

The above object is further achieved by an X-ray apparatus for determining the distributions of density and atomic number in an object to be examined, having an X-ray source for emitting X-radiation, an X-ray detector for detecting the X-radiation emitted by the X-ray source, and for converting the X-radiation into electrical signals for further processing, and having a signal processing device for processing the electrical signals of the X-ray detector, the signal processing device using a method according to the invention to determine the distributions of density and atomic number in an object to be examined, on the basis of at least two distributions, recorded on the X-ray apparatus with different X-ray spectra, of an X-ray absorption of the object to be examined.

Furthermore, an object may be achieved by a computer software product for ascertaining the distributions of density and atomic number in an object to be examined, on the basis of at least two image data records, recorded for different X-ray spectra, of the distribution of X-ray absorption values in the object to be examined as claimed in a method according to the invention.

An embodiment of the present invention permits the calculation of the spatial distribution of the mean density $\rho(\vec{r})$ and the effective atomic number $Z(\vec{r})$ from an evaluation of the spectrally influenced measured data of an X-ray apparatus. This yields novel contrasts, in particular with reference to the chemical and physical composition of the object to be examined. This functional display, hitherto reserved for magnetic resonance systems, of an object to be examined opens up a multiplicity of novel applications for X-ray diagnostics, and also for X-ray inspection technology.

For example, the display of the distribution of the atomic number in tissue etc. permits insight into the biochemical composition of an object to be examined, contrasts based on the chemical structure in organs previously displayed with homogeneous density, a quantitative determination of body constituents such as, for example, iodine or the like, and a demarcation of calcifications based on the atomic number. The isolated density display of an object permits an accurate determination of the centroid and density of objects such as is undertaken, for example, in the case of osteoporosis, inter alia.

In the field of safety technology, this means a more reliable detectability of dangerous components, in particular of explosive substances. In materials testing, access is opened up to the quantitative examination of the material composition and of the density distribution in the test specimens.

The determination of the functional dependence of the X-ray absorption values on density and atomic number for at least one X-ray spectrum is advantageously performed by means of reference measurement on a calibration sample and/or in the form of a simulation based on a physical model such that an installation-specific dependence of an X-ray absorption value on density and atomic number is obtained.

A transformation of the distributions of the X-ray absorption values into a distribution of the density and a distribution of the atomic number is preferably undertaken for each of the assigned X-ray absorption values of the first distribution of the X-ray absorption values and of the further distributions of the X-ray absorption values. This is done on the basis of the ascertainment of a value pair for density and atomic number such that the value pair fulfils the specific functional dependences of the X-ray absorption on density and atomic number for the first X-ray spectrum and at least one further X-ray spectrum. It is thereby possible to calculate density and atomic number for a pixel simply as cut-set of the functional dependences of the mutually assigned X-ray absorption values of the recorded distributions of the X-ray absorption values.

The first X-ray spectrum advantageously has a quantum energy that promotes an X-ray absorption relative to the quantum energy of the second X-ray spectrum by the photoelectric effect, such that a high resolution in the determination of the atomic numbers is obtained.

In a preferred embodiment of the present invention, at least one operating parameter of the X-ray tube is varied in order to vary an X-ray spectrum for recording the object to be examined, in which case the X-ray source emits a first X-ray spectrum in a first operating state and a second X-ray spectrum, differing therefrom, in a second operating state, such that a rapid alternation between two X-ray spectra is enabled.

Furthermore, a variation to the detector characteristic is advantageously undertaken in order to vary an X-ray spectrum for recording the object to be examined, the X-ray detector converting spectral subregions of the X-radiation received from the X-ray source into mutually independent electrical signals, and in the process permitting simultaneous recording of distributions of the X-ray absorption for different X-ray spectra.

Furthermore, the recording of at least one subregion of the object to be examined is advantageously performed with an increased X-ray dose so that a satisfactory resolution of the distribution of density and/or atomic number is achieved for this subregion without imposing an increased X-ray dose over the entire zone to be examined and, for example, exposing a patient to a high radiation load.

In order to record a first distribution of an X-ray absorption of the object to be examined, it is possible in accordance with an advantageous development to introduce into the beam path of the X-radiation a material that is not introduced into the beam path of the X-radiation in order to record a second distribution of an X-ray absorption of the object to be examined. Spectral components of the X-radiation that are specific to the material respectively used can thereby be filtered out when recording the first attenuation value distribution upstream and downstream of the object to be examined, thus achieving a high sensitivity in detecting a substance in the object to be examined that corresponds to this material.

BRIEF DESCRIPTION OF THE DRAWINGS

Further advantages, features and details of the invention will become evident from the description of illustrated embodiments given hereinbelow and the accompanying drawings, which are given by way of illustration only and thus are not limitative of the present invention, wherein:

FIG. 3a shows a flowchart of the methods of calculation according to an embodiment of the invention for the purpose of ascertaining isoabsorption lines.

DETAILED DESCRIPTION OF THE PREFERRED EMBODIMENTS

Figure 1:
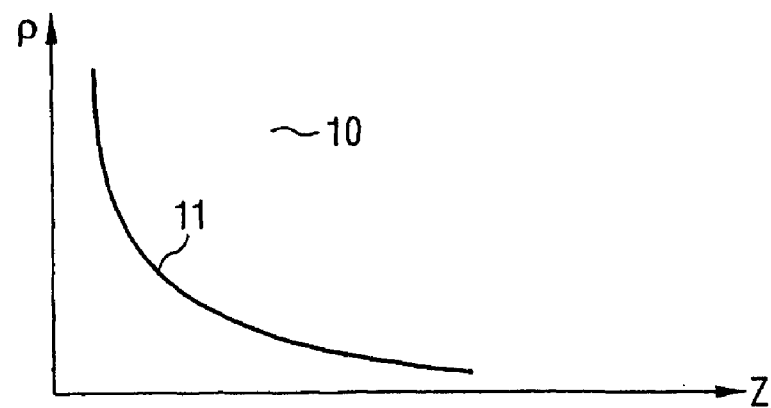
FIG. 1 shows with the aid of an isoabsorption line the production of identical attenuation values μ for materials of different composition.

The isoabsorption line 11 of diagram 10 of FIG. 1 connects all value pairs (ρ, Z) having an attenuation value μ or C identical for a defined X-ray spectrum. The illustration of FIG. 1 makes clear that information on the nature and composition of a tissue or material cannot be derived solely on the basis of the attenuation values of an X-ray image. Usually, in order to identify types of tissue in the X-ray image, a radiologist makes use of his anatomical knowledge and looks for irregularities on this basis. In order to clarify the identity of the irregularities, a medical practitioner is then forced in turn to appeal to empirical values and morphological criteria. Similarly, a person skilled in the art of materials testing and safety testing will base his judgment of the radiographic finding on his store of professional experience.

Figure 2:
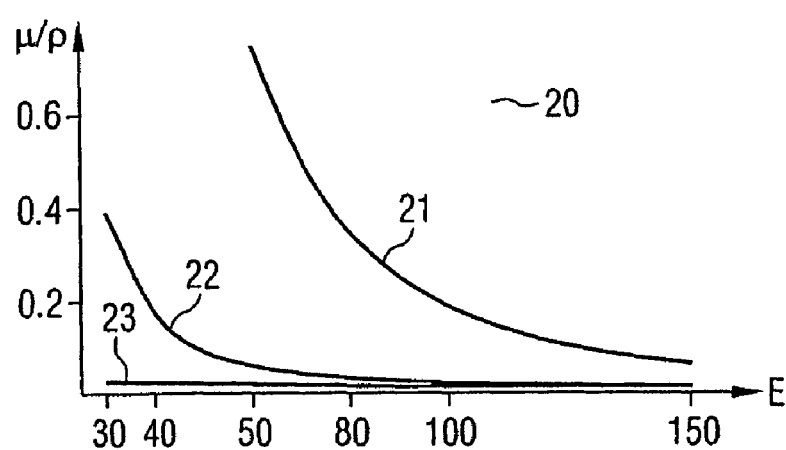
FIG. 2 shows the energy dependence of the X-ray attenuation for three elements.

X-radiation is attenuated to a greater or lesser extent by different materials and as a function of the energy of the X-radiation. FIG. 2 illustrates this with the aid of the energy dependence 20 of the mass attenuation coefficient for water 23, calcium 22 and iodine 21. This is to be ascribed to differently acting attenuation mechanisms for the various materials. In the diagnostically relevant energy range of the X-radiation, the X-ray attenuation is to be ascribed substantially to the absorption, caused by the photoelectric effect, and the scattering based on the Compton effect. The absorption is relevant, in particular, given low energy of the X-radiation and in the case of tissues with a high atomic number. The scattering is weakly dependent on the energy of the X-radiation, and is substantially dependent on the electron density, mediated via the physical density of the tissue.

The effective atomic number Z, entitled atomic number for simplicity in the context of this description, of a specific type of tissue is calculated from the atomic numbers $Z_i$ of the elements participating in the structure, their atomic weights $A_i$ and their local material-equivalent densities $\rho_i$ as:

$$z = \left\{ \frac{\sum_i \frac{\rho_i}{A_i} \rho_i z_i^A}{\sum_i \frac{\rho_i}{A_i} \rho_i} \right\}^{\frac{1}{3}} \tag{3}$$

The result is $Z_{Ca}=20$, for pure calcium, approximately $Z_{CaH_2} \cong 16.04$ for calcium hydride, and approximately $Z_{H_2O} \cong 7.428$ for water. The chemical or else biological composition of an object can therefore be detected very effectively via the atomic number Z.

Calculating the atomic number distribution and density distribution in a zone to be examined requires at least two X-ray pictures of the zone that have an identical recording geometry but are produced using a different energy of the X-radiation applied. The Z-resolution and ρ-resolution can be improved by using more than two X-ray pictures recorded with the aid of different X-radiation energy, but this also increases the radiation load. Consequently, this option does not always obtain in the case of examining a patient.

The starting point in the conversion of image data based on attenuation value into distribution images of the atomic numbers and the density of material or tissue is knowledge of the isoabsorption lines for each X-ray spectrum of an X-ray apparatus. As already mentioned, X-ray spectrum is understood here not as the narrowly interpreted term of the spectral distribution of an X-radiation emitted by the X-ray source of the apparatus, but as an extended term that takes account of the different weightings of different spectral regions of the emission spectrum of the X-ray tube on the part of the X-ray detectors. A measured attenuation value is therefore yielded by the direct attenuation of the radiation spectrum emitted by the X-ray tube, and the spectral efficiency of the X-ray detector used. The two values are installation-specific variables and must be ascertained either directly or indirectly by means of the attenuation values of calibration samples. They are the basis for calculating the isoabsorption lines.

FIG. 3a outlines three methods 300 for modeling and for calculating a family of iso-absorption lines, which are selectable in step 301, specifically a theoretical modeling, an experimental determination and a theoretical modeling with a calibration of the curves by means of experimentally determined parameters.

In principle, as many isoabsorption lines are to be determined as there are required attenuation values to cover the range of X-ray attenuations in the X-ray pictures. In this process, there is no need to calculate an isoabsorption line for each theoretically occurring attenuation value; if required, isoabsorption lines not calculated can be made available by interpolation or other suitable averaging methods.

The basic steps of the theoretical modeling are illustrated in the left-hand branch of the flowchart of FIG. 3a. Firstly, in step S302 the data of the for an installation-specific X-ray emission spectra S(E) are input with the tube voltages as parameter. For this purpose, the spectral distributions of the X-radiation can be gauged experimentally in advance for each individual X-ray installation, or use is made of the data characteristic of a specific type of X-ray source. The detector apparatus function w(E) is ascertained in step S303. It is also possible for this purpose firstly to undertake an accurate measurement of the detector arrangement, or else use is made of the data characteristic of the detector type such as, for example, the spectral technical specification thereof. The calculation of the isoabsorption lines in the form of families of curves $C_i(\rho, Z)$ and $\mu_i(\rho, Z)$, respectively, is undertaken in step S304 on the basis of a physical model that simulates the X-ray attenuations $C_i$ and $\mu_i$ for materials with different atomic numbers and given different material densities for each relevant combination of S(E) and w(E).

The families of curves of the isoabsorption lines can also be determined experimentally as an alternative to the theoretical modeling of steps S302 to S304. For this purpose, the X-ray attenuations of calibration materials of different density and mean atomic number are measured in the X-ray apparatus for various relevant combinations of S(E) and w(E) in step S305. The measured values form the interpolation points for the subsequent calculation of the families of curves of isoabsorption lines $C_i$ and $\mu_i$, respectively, in step S306.

As a further alternative, the families of curves $C_i$ and $\mu_i$, respectively, modeled on a theoretical basis can be calibrated with the aid of experimentally ascertained X-ray attenuation values. The attenuation values required for calibrating the theoretical families of curves are measured in step S307, as described above for step S305, with the aid of suitable calibration materials and/or phantoms in the X-ray installation. By contrast with the purely theoretical modeling of steps S302 to S304, in this method the exact knowledge of the X-ray emission spectra S(E) and w(E) is not a precondition, but a parameter of the theoretical modeling of the families of curves of isoabsorption lines $C_i$ and $\mu_i$, respectively, in step S308. The calibration of the curves in step S309 with the aid of the calibration values ascertained experimentally in step S307 finally defines values for these parameters that are specific to the X-ray emission spectra and detector apparatus functions of the X-ray apparatus.

Ascertaining the isoabsorption lines for the required X-ray attenuation values and combinations of S(E) and w(E) provides the preconditions for a transformation of image data that represent attenuation values for the X-radiation in the case of passage through a tissue into image data that represent a distribution of the atomic number or the material density in the corresponding tissue.

The three methods for determining isoabsorption lines can also be mixed depending on the task set. For example, it is possible for values that can be determined experimentally only inaccurately or only with great outlay, or even not at all, to be supplemented with the aid of a theoretical modeling, or to be rendered more accurate. The data derived with the aid of different methods are then combined in step S310 to form a standard data record and are held ready in step S311 for the image transformations.

Figure 3B:
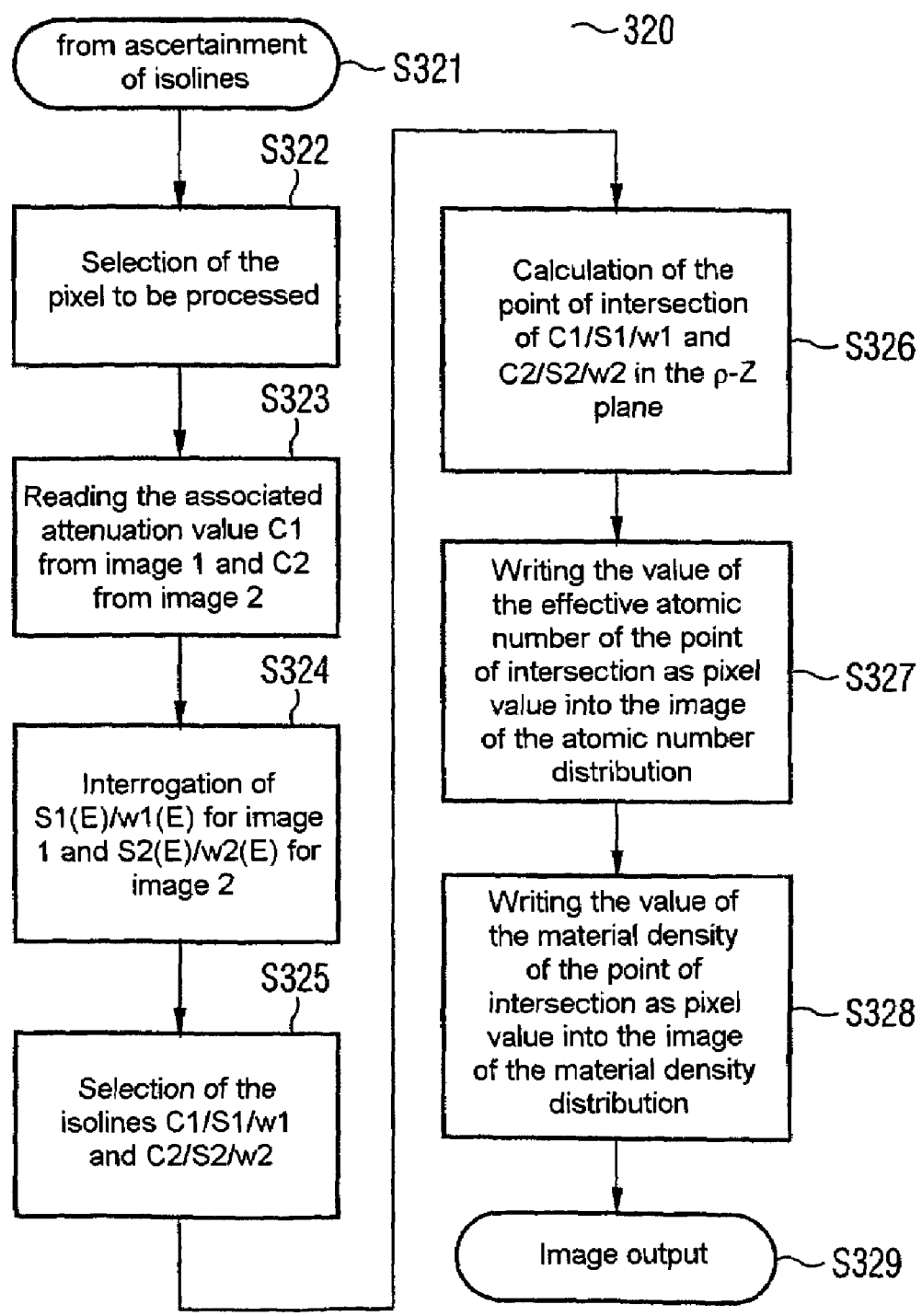
FIG. 3b shows a flowchart of the transformation of the X-ray absorption values into values of material density and atomic number.

The transformation method 320 according to an embodiment of the invention is illustrated in FIG. 3b. It is based on the families of curves of isoabsorption lines determined according to one of the previously described methods 300 and held ready as data record in step S321.

A transformation is performed in a pixelwise fashion.

What follows proceeds from a transformation of a distribution of X-ray absorption values based on two X-ray images recorded for different X-radiation spectra but an identical recording geometry. This is the minimum precondition for carrying out a transformation according to the invention. However, it is also possible to make use of more than two X-ray pictures given more than two different energy distributions of the X-radiation.

The selection of a pixel to be transformed is made in step S322, and the attenuation values $C_1$ and $\mu_1$, respectively, for this pixel are read out of the first X-ray image, and $C_2$ and $\mu_2$, respectively, are read out of the second x-ray image in the following step S323. The interrogation of the X-ray spectrum $S_1(E)$ used for the first X-ray picture, and of the detector apparatus functions $w_1(E)$ as well as the corresponding values $S_2(E)$ and $w_2(E)$ for the second X-ray image, is performed in the subsequent step S324. These values form the parameters for a subsequent selection of the isoabsorption lines to be assigned to the respective attenuation values. The spectral distributions $S_i(E)$ and $w_i(E)$, respectively, can also be ascertained indirectly here, for example via an interrogation of the tube voltages $U_1$ and $U_2$, respectively, used and/or of the operating parameters of the X-ray detectors.

Figure 4:
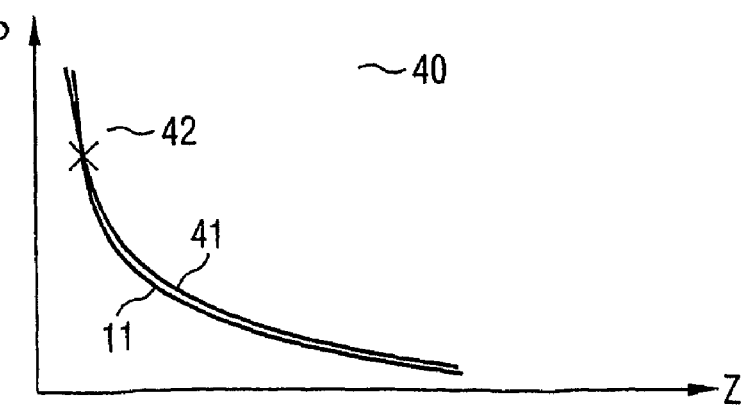
FIG. 4 shows two isoabsorption lines of a type of tissue for two different X-ray spectra.

A first curve, which fulfils the conditions $C_1$ and $\mu_1$, respectively, in the case of the parameters $S_1(E)$ and $w_1(E)$, and a second curve, which fulfils the conditions $C_2$ and $\mu_2$, respectively, in the case of the parameters $S_2(E)$ and $w_2(E)$ are selected in step S325 from the data record of isoabsorption lines that is held ready in step S321. An example of a first isoabsorption line 11, and of a second one 41, obtained in such a way as illustrated in the graphical representation 40 of FIG. 4.

The point of intersection 42 is calculated in step S326 of the transformation method 320 as cut-set of two curves 11 and 41. The curve intersection 42 can be ascertained, for example, by a local linear transformation or by finding the point of intersection iteratively. Since the two curves 11 and 41 represent two different attenuation values for the same pixel and, therefore, for an identical subregion of a tissue to be examined, the two attenuation values must be caused by the same type of material or tissue. The coordinates (ρ, Z) of the point of intersection 42 of the curves therefore reproduce the material density and the atomic number of the tissue subregion to be assigned to the pixel.

Finally, the atomic number Z thus ascertained is written in step S327 into the atomic number distribution as corresponding pixel value, and into the density distribution in step S328 by analogy with the material density value ρ ascertained. The steps S322 to S328 are repeated for all remaining pixels until it is finally possible to output the image in step S329. It is possible to skip step S324 in this process, since the spectral distributions $S_i(E)$ and $w_i(E)$, respectively, are identical for all pixels of an image.

The accuracy of the determination of the density ρ and the atomic number Z is influenced substantially by the noise component of the attenuation values, and by the spectral resolution of the measurement. The noise component can be influenced, for example, via the X-ray dose used. The spectral resolution is a function of the spacing and of the width of the X-ray spectra used for the measurement.

In general, in the case of X-ray spectra of relatively low energy, the result is a preference for X-ray attenuation by the photoelectric effect, while for X-ray spectra of relatively high energy it is a preference for X-ray attenuation by the Compton effect. Putting it more accurately, the influence of the atomic number on the X-ray attenuation values of a picture is relatively greater for lower X-ray energy than for higher X-ray energy. The influence of a material density or tissue density on the X-ray attenuation values behaves in an exactly opposite fashion, by contrast. Consequently, it is advantageous initially to select a first X-ray spectrum such that a substantial fraction of the first X-ray attenuation values stems from the influence of the atomic numbers of the tissue or material examined, and a second X-ray spectrum is then selected such that the densities of the object to be examined exert a substantial influence on the second X-ray attenuation values.

Consequently, quantum energies of the X-ray spectra in the range between 50 keV and 120 keV are preferred for computed tomography (CT), and so it is possible to select an adequate energy spacing between a first and a second X-ray spectrum without the need to increase the X-ray dose in ranges injurious to patients. The lower energy range can even be fixed at 10 keV and 1 kev, respectively, in mammography and micro-CT.

Higher X-ray doses are used in materials testing and safety testing than can be advocated in the examination of organisms. A mostly substantially better signal-to-noise ratio is obtained with these higher X-ray doses. Moreover, substantially higher X-ray energies of up to 1 MeV can also be used. Consequently, even if the atomic number contributes only a small fraction to the X-ray absorption for a given X-ray energy, its value can be determined with high accuracy nevertheless, if the noise component of the X-ray absorption values is substantially smaller for the X-ray dose used than the relative fraction of the atomic number in the corresponding X-ray absorption values. Consequently, the emphasis is not so much on the absolute energy position of the X-ray spectra used, but on their different mutual energy position. The selection of the absolute positions is then influenced by the X-ray doses used and by the substances to be detected.

Adequate atomic number contrasts for a satisfactory insight into the chemical composition of a material, or the biochemical composition of a tissue, are set via the X-ray dose and the X-ray spectra used. The required resolution in the representation of the atomic number distribution is a function of the diagnostic formulation of the task. A quantitative measurement of typical body constituents such as, for example, iodine, magnesium, carbon, nitrogen, oxygen, sodium, phosphorus, sulfur, chlorine, potassium, manganese, iron, cobalt, copper, zinc, selenium, molybdenum or the like requires a Z-resolution different from that for obtaining a chemical contrast based on, for example, the iron content in a liver. The requirements placed on a Z-resolution for demarcating objects from an environment with a greatly differing atomic number are relatively relaxed. In principle, the Z-resolution must be better than the difference between the atomic numbers still to be distinguished. A Z-resolution of up to 0.1 can be achieved at present.

The density distribution can be evaluated for the purpose of measuring the weighting distribution of an object in accordance with the equation $$m(\vec{r}) = \rho(\vec{r}) \times \Delta v(\vec{r}) \qquad (4)$$

and can be used to determine the centroid. Applications are, for example, the measurement of the density of bones or of the brain, but also the determination of the actual centroid of an object under test.

In order to classify and demarcate body materials such as, for example, liver, kidneys, white and gray brain matter etc. or material classes, it is possible to undertake a combined evaluation of the distributions of atomic number and density by undertaking windowing of the density and of the type of tissue or material determined via the atomic number. In addition to demarcating a for example malignant tissue, this method can also be used at the same time, for example, to determine the nitrogen content thereof, and for planning the dose in a subsequent radiation therapy.

In order to enable a comparison with classical radiography that represents attenuation values, the original images can also continue to be represented as standard X-ray images. If these are no longer available, it is possible to back-calculate a downward-compatible standard X-ray image from the distribution of atomic number and density for an object to be examined.

In the case of the detector noise of X-ray imaging systems that is high by comparison with computed tomography, the dynamics of the X-ray image contrasts is reduced, and therefore so are the Z-resolution and ρ-resolution that can be achieved. In some circumstances, the stipulation of a high Z-resolution or ρ-resolution during an examination of a large surface would signify an impermissibly high dose burden. Consequently, after the overview measurements a second measurement is undertaken with an increased dose in accordance with the diagnostic requirements in a relatively small zone to be examined. This method is to be recommended in mammography for the purpose of examining microcalcifications.

Three different X-ray systems are shown in FIG. 5 for the purpose of illustrating three basic principles of radioscopy methods.

Figure 5A:
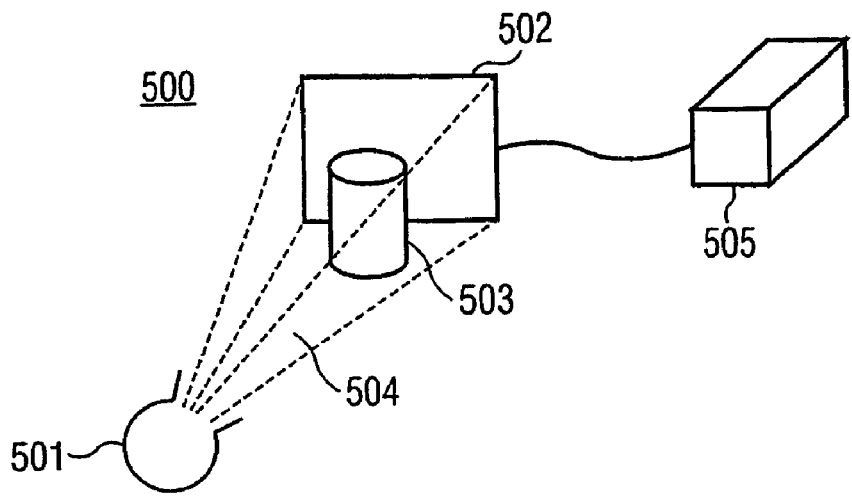
FIG. 5 shows a diagram of three typical X-raying techniques.

FIG. 5a shows an X-ray imaging system 500 for projectively imaging an object to be examined 503 onto a two-dimensional area detector 502 connected to signal processing device 505 for processing the electrical signals of the X-ray detector 502. A patient 503 or an object 503 is generally located therein at rest relative to the arrangement of X-ray tube 501 and detector 502 in the course of X-ray imaging.

Figure 5B:
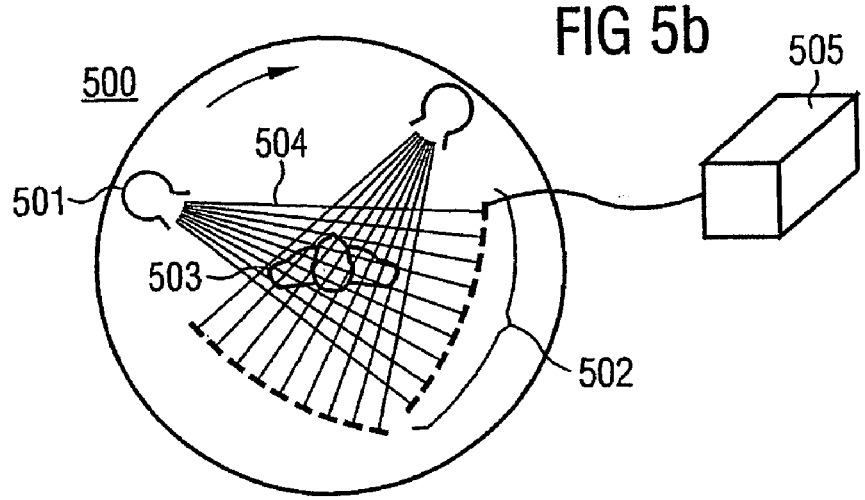

As an example of a computed tomography apparatus, FIG. 5b reproduces in a diagram the principle of a fan-beam unit 500 with a rotating detector system 502. The X-ray beams are emitted in the shape of a fan by the X-ray tube 501. They further transilluminate the object to be examined 503 from a specific angular position, and finally strike a line-shaped arrangement of discrete detectors. A recording cycle comprises a multiplicity of such transilluminations at different angular positions relative to the object to be examined.

Figure 5C:
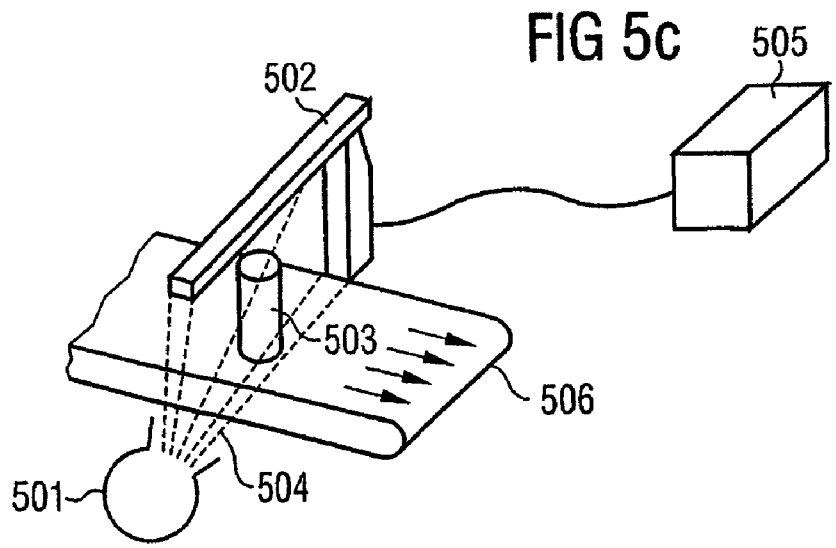

In the case of the type of fluoroscopic apparatus 500 illustrated in FIG. 5c, the object to be investigated 503 is guided to the installation through the beam path 504 with the aid of a transport apparatus such as, for example, a conveyor belt 506. This type of X-ray apparatus is used mainly in safety testing. A line-shaped, one-dimensional detector, frequently an L-shaped one, is used as detector. When passing through the beam path 504, the object 503 is scanned in a linewise fashion by X-rays emitted by the X-ray tube 501, and a complete fluoroscopic image of the object is compiled from the image rows thus produced.

FIG. 6 shows various possibilities of influencing the effective X-ray spectrum such as is yielded from the interaction of the radiation distribution 610 (611) emitted by the X-ray tube 501, and the spectral characteristic of the detector apparatus function 612 (620).

Figure 6A:
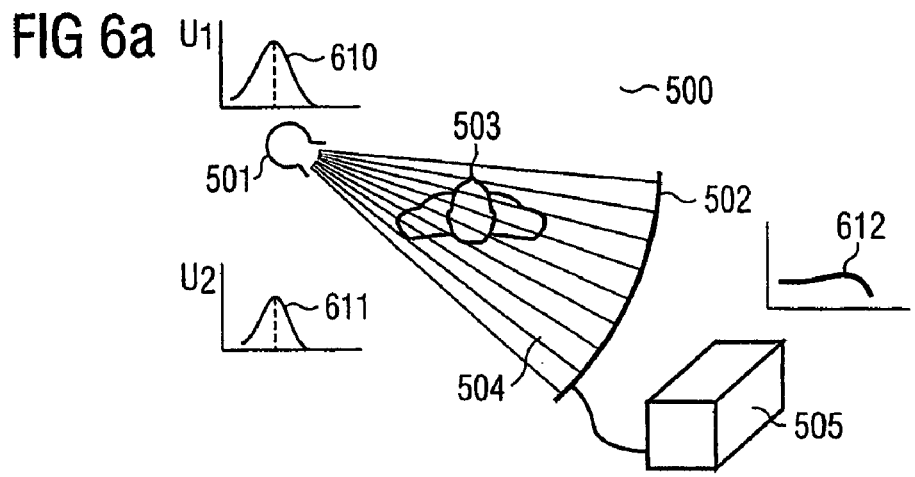
FIG. 6 shows a diagram of different methods for varying the X-ray spectra.

FIG. 6a illustrates a rapid changeover of the tube voltage from a value $U_1$ to a value $U_2$ so as to achieve an alternation between two X-ray emission spectra 610 and 611. It is advantageous to record each partial recording of a recording cycle firstly at one of the two tube voltages and, immediately thereafter, at the other of the two tube voltages, in order to minimize artifacts owing to movements, for example, of a patient during the recording cycle. In the case of X-ray apparatuses 500 with short measuring times such as, for example, X-ray projection systems, it is also possible for each recording cycle to be run through completely for one of the two tube voltages, in each case. Instead of changing over the tube voltage, it is also possible to introduce filters or filter systems between the X-ray tube and the object to be examined or between the object to be examined and the X-ray detector, in order to influence the X-ray spectrum. The operation of the X-ray tube at an operating voltage $U_1$ is then replaced by an operation at a standard operating voltage and the use of no or a first filter or filter system; operation at $U_2$ is replaced by the use of a second filter or filter system.

Figure 6B:
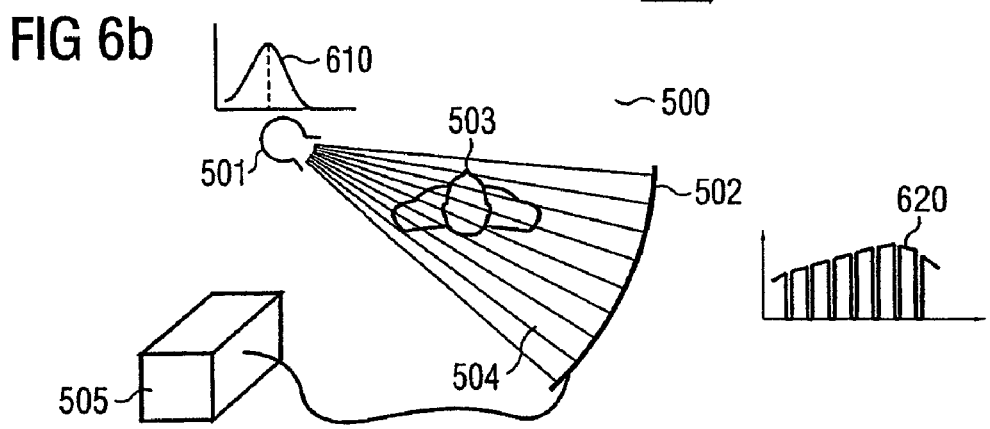

Since an X-ray tube 501 does not emit monoenergetic radiation but a relatively broad spectrum of X-radiation 504, it is possible, as shown in FIG. 6b, in one measuring operation to obtain several pictures for different X-ray spectra by using an energy-sensitive detector 620. The latter supplies separate measuring signals for, in general, spectral regions arranged next to one another. Attenuation values are thus obtained simultaneously for different, mutually separate spectral regions of the X-ray spectrum, that is to say in a recording cycle a number, defined by the embodiment and wiring of the detector, of X-ray images for different radiation energies. Such detectors 620 can be implemented as layer structure detectors, use being made of the fact that the depth of penetration of X-radiation into the layer system of the detector is determined by the energy of the X-ray quanta. It is also possible to use quantum counters as energy-sensitive detectors as an alternative to layer detectors.

Figure 6C:
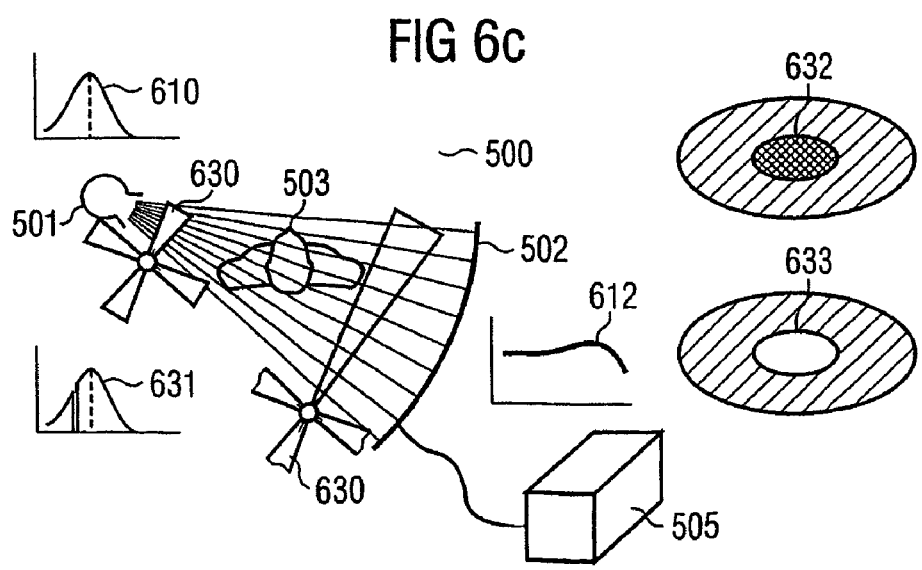

FIG. 6c shows a third variant for influencing the X-ray emission spectrum. Here, a material 630 of an installation-specific element is placed, for example in the form of rapidly rotating filter wheels 630, between an X-ray tube 501 and an object to be examined 503, or between an object to be examined 503 and an X-ray detector 502. Each element absorbs X-radiation in a characteristic way 631 and in a likewise characteristic spectral region. If a wing of the filter wheel is located in the beam path, a spectral region typical of this element is attenuated in the beam path or, in the most favorable case, eliminated. A measurement, with and without a filter wheel wing in the beam path, are now undertaken for each partial recording of a recording cycle. An element in the object to be examined that corresponds to the filter wheel element can then exhibit an X-ray attenuation value 632 only in the measurements without filter wheel covering of the beam path. In the other case, the measured attenuation value 633 is ideally equal to zero. It is possible in this way to detect with high precision the presence or absence of a specific element such as, for example, iron or copper in an object to be examined. This detection method is important in particular in mammography and materials testing.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for determining distributions of density and atomic number in an object to be examined, comprising:
   recording a first distribution of X-ray absorption values of the object to be examined using a first X-ray spectrum;
   recording at least a further distribution of X-ray absorption values of the object to be examined using a further X-ray spectrum;
   selecting, from the recorded first distribution of X-ray absorption values, a first X-ray absorption value;
   selecting from the recorded further distribution of X-ray absorption values, a further X-ray absorption value assigned to said first X-ray absorption value or selecting, from each of said recorded further distribution of X-ray absorption values, a further X-ray absorption value assigned to said first X-ray absorption value;
   specifying a first function representing paired values of density and atomic number that correspond to said first X-ray absorption value selected from said recorded first distribution of X-ray absorption values;
   specifying a further function representing paired values of density and atomic number that correspond to said further X-ray absorption value selected from said recorded further distribution of X-ray absorption values of specifying a further function representing paired values of density and atomic number for each X-ray absorption value assigned to said first X-ray absorption value in the recorded further distributions of X-ray absorption values; and
   determining a value for the density and determining a value for the atomic number from a comparison of said first function representing paired values of density and atomic number that correspond to said first X-ray absorption value with one or more of said further functions representing paired values of density and atomic number that correspond to said respective further X-ray absorption values, and which are assigned to said first X-ray absorption value.

2. The method as claimed in claim 1, wherein a function representing paired values of density and atomic number that correspond to a respective X-ray absorption value selected from said recorded first or further distribution of X-ray absorption values is specified based on a reference measurement on a calibration sample.

3. The method as claimed in claim 2, wherein a function representing paired values of density and atomic number that correspond to a respective X-ray absorption value selected from said recorded first or further distribution of X-ray absorption values is specified based on a simulation utilizing a physical model.

4. The method as claimed in claim 2, wherein a transformation of the distributions of the X-ray absorption values into corresponding distributions of density and atomic number is carried out for each of the first X-ray absorption values and the further X-ray absorption values assigned to the respective the first X-ray absorption values based on the determination of a paired value for the density and the atomic number such that a paired value of the first function is chosen, which corresponds to a paired value of a further function.

5. The method as claimed in claim 2, wherein the first X-ray spectrum has a quantum energy that results in a higher fraction of X-ray absorption based on the photoelectric effect when using a further X-ray spectrum.

6. The method as claimed in claim 2, wherein at least one of at least one operating parameter of the X-ray tube and the detector characteristic is varied in order to vary an X-ray spectrum for recording the object to be examined.

7. The method as claimed in claim 2, wherein at least a subregion of the object to be examined is recorded with an increased X-ray dose.

8. The method as claimed in claim 1, wherein a function representing paired values of density and atomic number that correspond to a respective X-ray absorption value selected from said recorded first or further distribution of X-ray absorption values is specified based on a simulation utilizing a physical model.

9. The method as claimed in claim 1, wherein a transformation of the distributions of the X-ray absorption values into corresponding distributions of density and atomic number is carried out for each of the first X-ray absorption values and the further X-ray absorption values assigned to the respective first X-ray absorption value based on the determination of a paired value for the density and the atomic number such that a paired value of the first function is chosen, which corresponds to a paired value of a further function.

10. The method as claimed in claim 1, wherein the first X-ray spectrum has a quantum energy that results in a higher fraction of X-ray absorption based on the photoelectric effect when using a further X-ray spectrum.

11. The method as claimed in claim 1, wherein at least one of at least one operating parameter of the X-ray tube and the detector characteristic is varied in order to vary an X-ray spectrum for recording the object to be examined.

12. The method as claimed in claim 1, wherein at least a subregion of the object to be examined is recorded with an increased X-ray dose.

13. A computer-readable medium having code portions embodied thereon that, when read by a computer device, cause the computer device to perform the method of claim 1.

14. An X-ray apparatus for determining distributions of density and atomic number in an object to be examined, comprising:
an X-ray source adapted to emit X-radiation;
an X-ray detector adapted to detect the X-radiation emitted by the X-ray source and to convert the X-radiation into electrical signals for further processing; and
a signal processing device, adapted to process the electrical signals of the X-ray detector, wherein the signal processing device is adapted to determine distributions of density and atomic number in an object to be examined on the basis of a first and at least one further distribution of X-ray absorption values of the object to be examined recorded on the X-ray apparatus with different X-ray spectra such that, a value for the density and a value for the atomic number are determined for each absorption value of a first distribution of X-ray absorption values recorded with a first X-ray spectrum by
specifying a first function representing paired values of density and atomic number that correspond to an X-ray absorption value from said recorded first distribution of X-ray absorption values and specifying an at least second function representing paired values of density and atomic number that correspond to a further X-ray absorption value of the at least one further distribution of X-ray absorption values and that is further assigned to said absorption value of the first distribution of X-ray absorption values; and by
comparing the first function with the at least second function to obtain a paired value for density and atomic number common to the first and the at least second function.

15. The X-ray apparatus as claimed in claim 14, wherein the X-ray source is adapted to emit a first X-ray spectrum in a first operating state and a second X-ray spectrum, different from the first operating state, in a second operating state.

16. The X-ray apparatus as claimed in claim 15, wherein the X-ray detector is adapted to convert spectral subregions of the X-radiation received from the X-ray source into mutually independent electrical signals.

17. The X-ray apparatus as claimed in claim 15, wherein a material is adapted to be introduced into the beam path of the X-radiation to record a first distribution of an X-ray absorption of the object to be examined, and no corresponding material is introduced into the beam path of the X-radiation to record a second distribution of an X-ray absorption of the object to be examined.

18. The X-ray apparatus as claimed in claim 14, wherein the X-ray detector is adapted to convert spectral subregions of the X-radiation received from the X-ray source into mutually independent electrical signals.

19. The X-ray apparatus as claimed in claim 18, wherein a material is adapted to be introduced into the beam path of the X-radiation to record a first distribution of an X-ray absorption of the object to be examined, and no corresponding material is introduced into the beam path of the X-radiation to record a second distribution of an X-ray absorption of the object to be examined.

20. The X-ray apparatus as claimed in claim 14, wherein a material is adapted to be introduced into the beam path of the X-radiation to record a first distribution of an X-ray absorption of the object to be examined, and no corresponding material is introduced into the beam path of the X-radiation to record a second distribution of an X-ray absorption of the object to be examined.

21. An X-ray apparatus for determining distributions of density and atomic number in an object to be examined, comprising:
   means for emitting X-radiation;
   means for detecting the emitted X-radiation and for converting the X-radiation into electrical signals for further processing; and
   means for processing the electrical signals and for determining distributions of density and atomic number in an object to be examined, on the basis of a first and at least one further distribution of X-ray absorption values of the object to be examined, recorded on the X-ray apparatus with different X-ray spectra such that, a value for the density and a value for the atomic number are determined for each absorption value of a first distribution of X-ray absorption values recorded with a first X-ray spectrum by
      specifying a first function representing paired values of density and atomic number that correspond to an X-ray absorption value from said recorded first distribution of X-ray absorption values and specifying an at least second function representing paired values of density and atomic number that correspond to a further X-ray absorption value of the at least one further distribution of X-ray absorption values and that is further assigned to said absorption value of the first distribution of X-ray absorption values; and by
      comparing the first function with the at least second function to obtain a paired value for density and atomic number common to the first and the at least second function.

22. The X-ray apparatus as claimed in claim 21, wherein the means for emitting is for emitting a first X-ray spectrum in a first operating state and a second X-ray spectrum, different from the first operating state, in a second operating state.

23. The X-ray apparatus as claimed in claim 21, wherein the means for detecting is for converting spectral subregions of the X-radiation into mutually independent electrical signals.

24. The X-ray apparatus as claimed in claim 21, wherein a material is adapted to be introduced into the beam path of the X-radiation to record a first distribution of an X-ray absorption of the object to be examined, and no corresponding material is introduced into the beam path of the X-radiation to record a second distribution of an X-ray absorption of the object to be examined.

25. The X-ray apparatus as claimed in claim 21, wherein the means for emitting includes an x-ray source.

26. The X-ray apparatus as claimed in claim 21, wherein the means for detecting includes an x-ray detector.

27. A method for determining distributions of density and atomic number in an object to be examined, comprising:
   detecting emitted X-radiation;
   converting the X-radiation into electrical signals; and
   determining distributions of density and atomic number in an object to be examined on the basis of a first and at least one other distribution of X-ray absorption values of the object to be examined, recorded with different X-ray spectra such that, a value for the density and a value for the atomic number are determined for each absorption value of a first distribution of X-ray absorption values recorded with a first X-ray spectrum by
      specifying a first function representing paired values of density and atomic number that correspond to an X-ray absorption value from said recorded first distribution of X-ray absorption values and specifying an at least second function representing paired values of density and atomic number that correspond to a further X-ray absorption value of the at least one further distribution of X-ray absorption values and that is further assigned to said absorption value of the first distribution of X-ray absorption values; and by
      comparing the first function with the at least second function to obtain a paired value for density and atomic number common to the first and the at least second function.

28. A computer-readable medium having code portions embodied thereon that, when read by a computer device, cause the computer device to perform the method of claim 27.

29. A computer-readable medium having code portions embodied thereon that, when read by a computer device, cause the computer device to determine the distributions of density and atomic number in an object to be examined, on the basis of a first and at least one other image data record recorded for different distributions of X-ray absorption values in the object to be examined using at least a first and at least one other X-ray spectrum such that, a value for the density and a value for the atomic number are determined for each absorption value of a first distribution of X-ray absorption values by
   specifying a first function representing paired values of density and atomic number that correspond to an X-ray absorption value from said recorded first distribution of X-ray absorption values and specifying a further function representing paired values of density and atomic number that correspond to a further X-ray absorption value of the at least one further distribution of X-ray absorption values and that is further assigned to said absorption value of the first distribution of X-ray absorption values; and by
   comparing the first function with the further function to obtain a paired value for density and atomic number common to the first and the further function;
whereby a further function may be specified for each absorption value assigned to said absorption value of the first distribution of X-ray absorption values in each further distribution of X-ray absorption values of the object to be examined, and the corresponding density and atomic number be determined as the paired value for density and atomic number common to the first function and the further function or functions.

* * * * *